(12) United States Patent
Johnson et al.

(10) Patent No.: US 7,069,182 B2
(45) Date of Patent: Jun. 27, 2006

(54) DATABASE INTERPOLATION METHOD FOR OPTICAL MEASUREMENT OF DIFFRACTIVE MICROSTRUCTURES

(75) Inventors: Kenneth C. Johnson, Santa Clara, CA (US); Fred E. Stanke, Cupertino, CA (US)

(73) Assignee: Tokyo Electron Limited, Tokyo (JP)

( * ) Notice: Subject to any disclaimer, the term of this patent is extended or adjusted under 35 U.S.C. 154(b) by 0 days.

(21) Appl. No.: 11/212,165

(22) Filed: Aug. 26, 2005

(65) Prior Publication Data

US 2005/0280832 A1    Dec. 22, 2005

Related U.S. Application Data

(63) Continuation of application No. 10/777,353, filed on Feb. 12, 2004, now Pat. No. 6,950,780, which is a continuation of application No. 09/927,177, filed on Aug. 10, 2001, now Pat. No. 6,768,967.

(60) Provisional application No. 60/270,956, filed on Feb. 22, 2001, provisional application No. 60/224,451, filed on Aug. 10, 2000.

(51) Int. Cl.
*G01N 21/00* (2006.01)

(52) U.S. Cl. .......................... 702/182; 702/23; 702/32; 702/33; 702/40; 702/179; 356/432; 356/445

(58) Field of Classification Search ..................... None
See application file for complete search history.

(56) References Cited

U.S. PATENT DOCUMENTS

| | | | |
|---|---|---|---|
| 4,555,767 A | 11/1985 | Case et al. ................ 250/341.4 |
| 4,689,754 A | 8/1987 | Collins et al. ................. 702/32 |
| 4,757,207 A | 7/1988 | Chappelow et al. ..... 250/491.1 |
| 4,885,709 A | 12/1989 | Edgar et al. ................. 364/563 |
| 4,994,990 A | 2/1991 | Fujita et al. ................. 702/159 |
| 4,999,508 A | 3/1991 | Hyakumura ........... 250/559.27 |
| 5,000,573 A * | 3/1991 | Suzuki et al. ................ 356/490 |
| 5,262,635 A | 11/1993 | Curbelo .................... 250/214 R |
| 5,315,513 A | 5/1994 | Abreu et al. .................... 702/3 |
| 5,428,558 A | 6/1995 | Cahill et al. ................. 356/319 |
| 5,488,476 A | 1/1996 | Mansfield et al. ........... 356/512 |
| 5,502,799 A | 3/1996 | Tsuji et al. .................. 345/600 |
| 5,523,840 A | 6/1996 | Nishizawa et al. .......... 356/497 |
| 5,587,792 A | 12/1996 | Nishizawa et al. .......... 356/497 |
| 5,607,800 A | 3/1997 | Ziger ............................ 430/8 |
| 5,844,684 A * | 12/1998 | Maris et al. ................. 356/432 |
| 5,867,276 A | 2/1999 | McNeil et al. .............. 356/445 |
| 5,884,684 A | 3/1999 | Jefferson ..................... 356/432 |

(Continued)

FOREIGN PATENT DOCUMENTS

EP    72367 A    2/1983

(Continued)

OTHER PUBLICATIONS

G.H. Schut, "Review of Interpolation Methods for Digital Terrain Models," *The Canadian Surveyor*, vol. 30, No. 5, Dec. 1976, pp. 389-412.

(Continued)

*Primary Examiner*—Carol S. W. Tsai
(74) *Attorney, Agent, or Firm*—Stallman & Pollock LLP (57) ABSTRACT

A database interpolation method is used to rapidly calculate a predicted optical response characteristic of a diffractive microstructure as part of a real-time optical measurement process. The interpolated optical response is a continuous and (in a preferred embodiment) smooth function of measurement parameters, and it matches the theoretically-calculated optical response at the database-stored interpolation points.

17 Claims, 5 Drawing Sheets

U.S. PATENT DOCUMENTS

| | | | |
|---|---|---|---|
| 5,905,822 A | 5/1999 | Ito et al. | 382/300 |
| 5,963,329 A | 10/1999 | Conrad et al. | 356/372 |
| 5,993,386 A | 11/1999 | Ericsson | 600/300 |
| 6,008,906 A | 12/1999 | Maris | 356/432 |
| 6,037,614 A | 3/2000 | He et al. | 257/184 |
| 6,211,961 B1 | 4/2001 | Maris | 356/432 |
| 6,242,739 B1 | 6/2001 | Cherkassky | 250/339.11 |
| 6,281,974 B1 | 8/2001 | Scheiner et al. | 356/491 |
| 6,291,254 B1 | 9/2001 | Chou et al. | 438/18 |
| 6,340,602 B1 | 1/2002 | Johnson et al. | 438/7 |
| 6,476,920 B1 | 11/2002 | Scheiner et al. | 356/630 |
| 6,483,580 B1 | 11/2002 | Xu et al. | 356/300 |
| 6,485,872 B1 | 11/2002 | Rosenthal et al. | 430/30 |
| 6,489,801 B1* | 12/2002 | Borden et al. | 324/766 |
| 6,541,287 B1 | 4/2003 | Ino et al. | 438/16 |
| 6,542,829 B1 | 4/2003 | Gupta | 703/33 |
| 6,590,656 B1 | 7/2003 | Xu et al. | 356/369 |
| 6,780,657 B1 | 8/2004 | Ino | 438/14 |
| 6,801,326 B1 | 10/2004 | Finarov et al. | 356/630 |
| 6,819,426 B1 | 11/2004 | Sezginer et al. | 356/401 |
| 2004/0032582 A1* | 2/2004 | Johnson | 356/237.2 |
| 2004/0176928 A1* | 9/2004 | Johnson | 702/182 |
| 2005/0018190 A1* | 1/2005 | Sezginer et al. | 356/401 |

FOREIGN PATENT DOCUMENTS

| | | |
|---|---|---|
| EP | 324490 A | 7/1989 |
| JP | 08015036 A | 1/1996 |

OTHER PUBLICATIONS

W.S. Russell, "Polynomial Interpolation Schemes for Internal Derivative Distributions on Structured Grids," *Applied Numerical Mathematics*, vol. 17 (1995), pp. 129-171.

Book, *Numerical Recipes in C++—The Art of Scientific Computing*, Second Edition, Cambridge University Press (2002), pp. 126-132.

Printout, "GeoComputation 99—What's the Point? Interpolation and Extrapolation with a Regular Grid DEM,"(1999), 17 pages in length.

*IBM Technical Disclosure Bulletin*, "Spectroscopic Pitch Measurement Technique," Sep. 1989, pp. 391-392.

*IBM Technical Disclosure Bulletin*, "Phase-Sensitive Overlay Analysis Spectrometry," Mar. 1990, pp. 170-174.

D.M. Haaland et al., "Partial Least-Squares Methods for Spectral Analyses—1. Relation to Other Quantitative Calibration Methods and the Extraction of Qualitative Information," *Anal. Chemistry*, vol. 60, No. 11, Jun. 1, 1988, pp. 1193-1202.

R.H. Krukar et al., "Using Scattered Light Modeling for Semiconductor Critical Dimension Metrology and Calibration," *SPIE*, vol. 1926 (1993), pp. 60-71.

C.J. Raymond et al., "A Scatterometric Sensor for Lithography," *SPIE*, vol. 2336 (1994), pp. 37-49.

C.J. Raymond et al., "Metrology of Subwavelength Photoresist Gratings Using Optical Scatterometry," *J. Vac. Sci. Technology B*, vol. 13, No. 4, Jul./Aug. 1995, pp. 1484-1495.

M.R. Murnane et al., "Scatterometry for 0.24 μm—0.70 μm Developed Photoresist Metrology," *SPIE*, vol. 2439 (1995), pp. 427-436.

M.R. Murnane et al., "Subwavelength Photoresist Grating Metrology Using Scatterometry," *SPIE*, vol. 2532, (1995), pp. 251-261.

C.J. Raymond et al., "Multi-Parameter Process Metrology Using Scatterometry," *SPIE*, vol. 2638 (1995), pp. 84-93.

J. Bischoff et al., "Photoresist Metrology Based on Light Scattering," *SPIE*, vol. 2725 (1996), pp. 678-689.

C.J. Raymond et al., "Multi-Parameter CD Measurements Using Scatterometry," *SPIE*, vol. 2725 (1996), pp. 698-709.

C.J. Raymond et al., "Scatterometry for CD Measurements of Etched Structures," *SPIE*, vol. 2725 (1996), pp. 720-728.

B.K. Minhas et al., "Towards Sub—0.1 μm CD Measurements Using Scatterometry," *SPIE*, vol. 2725 (1996), pp. 729-739.

J. Bischoff et al., "Light Scattering Based Micrometrology," *SPIE*, vol. 2775 (1996), pp. 251-262.

X. Niu, "Specular Spectroscopic Scatterometry in DUV Lithography," *SPIE*, vol. 3677 (1999), pp. 159-168.

J. Allgair et al., "Manufacturing Considerations for Implementation of Scatterometry for Process Monitoring," *SPIE*, vol. 3998 (2000), pp. 125-134.

S.S.H. Naqvi et al., "Grating Parameter Estimation Using Scatterometry," *SPIE*, vol. 1992 (1993), pp. 170-180.

* cited by examiner

DATABASE INTERPOLATION METHOD FOR OPTICAL MEASUREMENT OF DIFFRACTIVE MICROSTRUCTURES

CROSS-REFERENCE TO RELATED APPLICATIONS

This application is a continuation of U.S. patent application Ser. No. 10/777,353, filed Feb. 12, 2004, now U.S. Pat. No. 6,950,780 which is in turn a continuation of U.S. patent application Ser. No. 09/927,177, filed Aug. 10, 2001, now U.S. Pat. No. 6,768,967 which also claims priority under 35 U.S.C. 119(e) from U.S. Provisional Application No. 60/224,451, "Method of Measuring Parameters of a Diffractive Structure Formed over a Substructure", filed Aug. 10, 2000, and U.S. Provisional Application No. 60/270,956, "Database Interpolation", filed Feb. 22, 2001, the disclosures of which are incorporated by reference.

TECHNICAL FIELD OF THE INVENTION

The present invention relates to optical measurement of parameters of interest on samples having diffractive structures thereon, and in particular relates to improvements in real-time analysis of the measured optical signal characteristics from a sample to determine parameter values for that sample.

BACKGROUND (This specification occasionally makes reference to prior published documents. A numbered list of these references can be found at the end of this section, under the sub-heading "References".)

In integrated circuit manufacture, the accurate measurement of the microstructures being patterned onto semiconductor wafers is highly desirable. Optical measurement methods are typically used for high-speed, non-destructive measurement of such structures. With such methods, a small spot on a measurement sample is illuminated with optical radiation comprising one or more wavelengths, and the sample properties over the measurement spot are determined by measuring characteristics of radiation reflected or diffracted by the sample (e.g., reflection intensity, polarization state, or angular distribution).

This disclosure relates to the measurement of a sample comprising a diffractive structure formed on or in a substrate, wherein lateral material inhomogeneities in the structure give rise to optical diffraction effects. If the lateral inhomogeneities are periodic with a period significantly smaller than the illuminating wavelengths, then diffracted orders other than the zeroth order may all be evanescent and not directly observable, or may be scattered outside the detection instrument's field of view. But the lateral structure geometry can nevertheless significantly affect the zeroth-order reflectivity, making it possible to measure structure features much smaller than the illuminating wavelengths.

A variety of measurement methods applicable to diffractive structures are known in the prior art. Reference 7 reviews a number of these methods. The most straightforward approach is to use a rigorous, theoretical model based on Maxwell's equations to calculate a predicted optical signal characteristic of the sample (e.g. reflectivity) as a function of sample measurement parameters (e.g., film thickness, linewidth, etc.), and adjust the measurement parameters in the model to minimize the discrepancy between the theoretical and measured optical signal (Ref's 10, 14). (Note: In this context the singular term "characteristic" may denote a composite entity such as a vector or matrix. The components of the characteristic might, for example, represent reflectivities at different wavelengths or collection angles.) The measurement process comprises the following steps: First, a set of trial values of the measurement parameters is selected. Then, based on these values a computer-representable model of the measurement sample structure (including its optical materials and geometry) is constructed. The electromagnetic interaction between the sample structure and illuminating radiation is numerically simulated to calculate a predicted optical signal characteristic, which is compared to the measured signal characteristic. An automated fitting optimization algorithm iteratively adjusts the trial parameter values and repeats the above process to minimize the discrepancy between the measured and predicted signal characteristic. (The optimization algorithm might typically minimize the mean-square error of the signal characteristic components.)

The above process can provide very accurate measurement capability, but the computational burden of computing the structure geometry and applying electromagnetic simulation within the measurement optimization loop makes this method impractical for many real-time measurement applications. A variety of alternative approaches have been developed to avoid the computational bottleneck, but usually at the expense of compromised measurement performance.

One alternative approach is to replace the exact theoretical model with an approximate model that represents the optical signal characteristic as a linear function of measurement parameters over some limited parameter range. There are several variants of this approach, including Inverse Least Squares (ILS), Principal Component Regression (PCR), and Partial Least Squares (PLS) (Ref's 1–5, 7, 11, 15). The linear coefficients of the approximate model are determined by a multivariate statistical analysis technique that minimizes the mean-square error between exact and approximate data points in a "calibration" data set. (The calibration data may be generated either from empirical measurements or from exact theoretical modeling simulations. This is done prior to measurement, so the calibration process does not impact measurement time.) The various linear models (ILS, PCR, PLS) differ in the type of statistical analysis method employed.

There are two fundamental limitations of the linear models: First, the linear approximation can only be applied over a limited range of measurement parameter values; and second, within this range the approximate model does not generally provide an exact fit to the calibration data points. (If the calibration data is empirically determined, one may not want the model to exactly fit the data, because the data could be corrupted by experimental noise. But if the data is determined from a theoretical model it would be preferable to use an approximation model that at least fits the calibration data points.) These deficiencies can be partially remedied by using a non-linear (e.g., quadratic) functional approximation (Ref. 7). This approach mitigates, but does not eliminate, the limitations of linear models.

Figure 1:
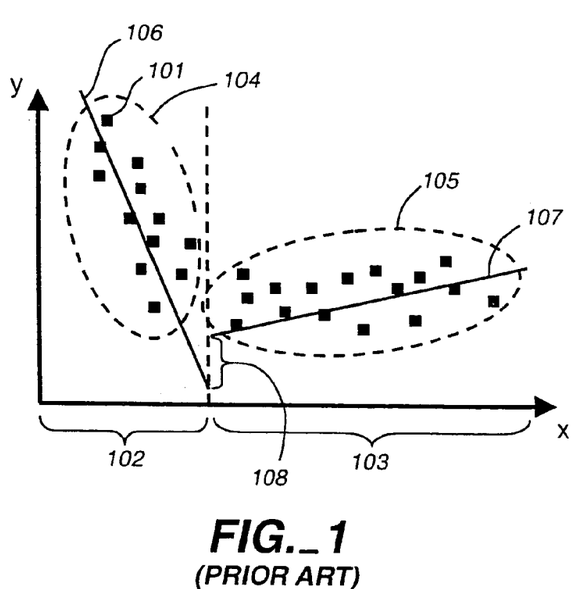
FIG. 1 illustrates the "range-splitting" method of the prior art.

The parameter range limit of functional (linear or non-linear) approximation models can be extended by the method of "range splitting", wherein the full parameter range is split into a number of subranges, and a different approximate model is used for each subrange (Ref. 7). The method is illustrated conceptually in FIG. 1 (cf. FIG. 2 in Ref. 7), which represents the relationship between a measurement parameter x, such as a linewidth parameter, and an optical signal characteristic y, such as the zeroth-order sample reflectivity at a particular collection angle and wavelength. (In practice one is interested in modeling the relationship between multiple measurement parameters, such as linewidths, film thicknesses, etc., and multiple signal components, such as reflectivities at different wavelengths or collection angles. However, the concepts illustrated in FIG. 1 are equally applicable to the more general case.) A set of calibration data points (e.g., point 101) is generated, either empirically or by theoretical modeling. The x parameter range is split into two (or more) subranges 102 and 103, and the set of calibration points is separated into corresponding subsets 104 and 105, depending on which subrange each point is in. A statistical analysis technique is applied to each subset to generate a separate approximation model (e.g., a linear model) for each subrange, such as linear model 106 for subrange 102 and model 107 for subrange 103.

Aside from the limitations inherent in the functional approximation models, the range-splitting method has additional deficiencies. Although the functional approximation is continuous and smooth within each subrange, it may exhibit discontinuities between subranges (such as discontinuity 108 in FIG. 1). These discontinuities can create numerical instabilities in optimization algorithms that estimate measurement parameters from optical signal data. The discontinuities can also be problematic for process monitoring and control because small changes in process conditions could result in large, discontinuous jumps in measurements.

Another drawback of the range-splitting model is the large number of required calibration points and the large amount of data that must be stored in the model. In the FIG. 1 illustration, each subrange uses a simple linear approximation model of the form $$y \cong a\, x + b \qquad \text{Eq. 1}$$

wherein a and b are calibration coefficients. At least two calibration points per subrange are required to determine a and b (generally, more than two are used to provide good statistical sampling over each subrange), and two coefficients (a and b) must be stored for each subrange. If there are M subranges the total number of calibration points must be at least 2 M, and the number of calibration coefficients is 2 M. Considering a more general situation in which there are N measurement parameters $x_1, x_2, \ldots x_N$, the linear approximation would take the form $$y \cong a_1 x_1 + a_2 x_2 + \ldots a_N x_N + b \qquad \text{Eq. 2}$$

Figure 2:
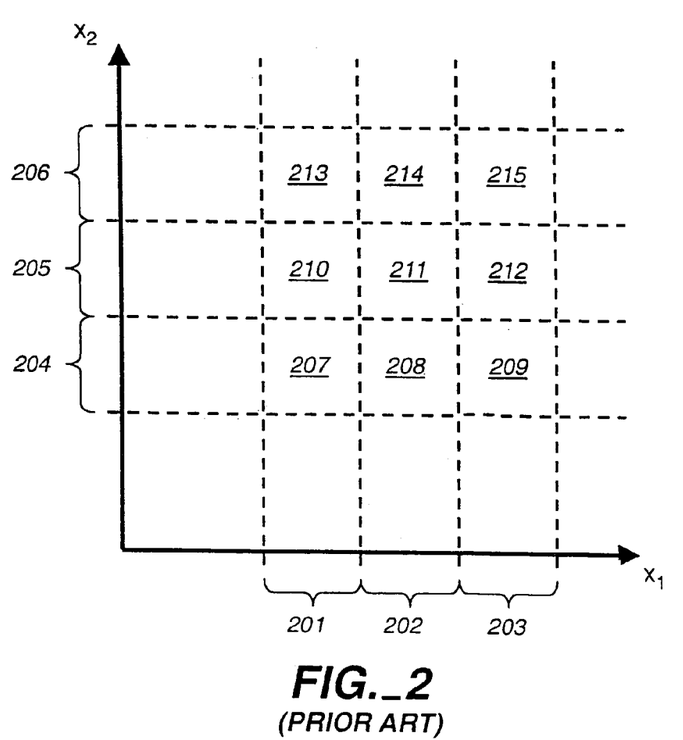
FIG. 2 illustrates a two-dimensional parameter space.

If the range of each parameter is split into M subranges, the number of separate linear approximation models required to cover all combinations of parameter subranges would be $M^N$, and the number of calibration parameters per combination $(a_1, a_2, \ldots, a_N, b)$ would be N+1. Thus the total number of calibration coefficients (and the minimum required number of calibration data points) would be $(N+1) M^N$. For example, FIG. 2 illustrates a parameter space spanned by two parameters, $x_1$ and $x_2$. The $x_1$ range is split into three subranges 201, 202, and 203, and the $x_2$ subrange is split into three subranges 204, 205, and 206. For this case, N=2, M=3, the number of $x_1$ and $x_2$ subrange combinations 207 . . . 215 is $3^2=9$, and the number of linear calibration coefficients would be $(2+1) 3^2=27$. Generalizing further, if the optical signal characteristic (y) comprises multiple signal components (e.g., for different wavelengths), the number of calibration coefficients will increase in proportion to the number of components. Furthermore, if a nonlinear (e.g., quadratic) subrange model is used, the number of calibration points and coefficients would be vastly larger.

Another measurement approach, Minimum Mean Square Error analysis (MMSE, Ref's 2–9, 11, 13, 15), provides a simple alternative to the range splitting method described above. With this approach, a database of pre-computed theoretical optical signal characteristics representing a large variety of measurement structures is searched and compared to a samples' measured optical signal, and the best-fitting comparison (in terms of a mean-square-error fitting criterion) determines the measurement result. (The above-noted references relate primarily to scatterometry and spectroscopy, but MMSE-type techniques have also been applied in the context of ellipsometry; see Ref's. 12 and 16.) The MMSE method is capable of modeling strong nonlinearities in the optical signal. But this method, like range-splitting, can exhibit problematic discontinuities in the measurement results due to the database's discrete parameter sampling.

All of these prior-art methods entail a compromise between measurement resolution and accuracy. The MMSE approach is not limited by any assumed functional form of the optical signal, and can therefore have good accuracy. But measurement resolution is fundamentally limited by the parameter sampling density. The functional approximation models, by contrast, are capable of "interpolating" between calibration data points, in the sense that the modeled signal is a continuous and smooth function of measurement parameters across the calibration range; hence such models can have essentially unlimited measurement resolution. However, the term "interpolation" is a misnomer in this context because the functional models do not accurately fit the calibration data points, and their accuracy is limited by the misfit. (For example, Ref. 11 reports a fit accuracy of 5–10 nm for linewidth and thickness parameters.)

REFERENCES

1. R. H. Krukar et al, "Using Scattered Light Modeling for Semiconductor Critical Dimension Metrology and Calibration," SPIE 1926, pp. 60–71 (1993).

2. C. J. Raymond et al, "A scatterometric sensor for lithography," SPIE Proc. 2336, pp. 37–49 (1994).

3. C. J. Raymond et al, "Metrology of subwavelength photoresist gratings using optical scatterometry," J. Vac. Sci. Technol. B, Vol. 13(4), pp. 1484–1495 (1995).

4. M. R. Murname et al, "Scatterometry for 0.24 um–0.70 um developed photoresist metrology," SPIE Proc. 2439, pp. 427–436 (1995).

5. M. R. Murname et al, "Subwavelength photoresist grating metrology using scatterometry," SPIE Proc. 2532, pp. 251–261 (1995).

6. C. J. Raymond et al, "Multi-parameter process metrology using scatterometry," SPIE Proc. 2638, pp. 84–93 (1995).

7. J. Bischoff et al, "Photoresist metrology based on light scattering," SPIE Proc. 2725, pp. 678–689 (1996).

8. C. J. Raymond et al, "Multi-parameter CD measurements using scatterometry," SPIE Proc. 2725, pp. 698–709 (1996).

9. C. J. Raymond et al, "Scatterometry for CD measurements of etched structures," SPIE Proc. 2725, pp. 720–728 (1996).

10. B. K. Minhas et al, "Towards sub-0.1 um CD measurements using scatterometry," SPIE Proc. 2725, pp. 729–739 (1996).

11. J. Bischoff et al, "Light scattering based micrometrology," SPIE Proc. 2775, pp. 251–259 (1996).

12. Xinhui Niu, "Specular Spectroscopic Scatterometry in DUV Lithography," SPIE 3677, pp. 159–168 (1999).

13. J. Allgair et al, "Manufacturing Considerations for Implementation of Scatterometry for Process Monitoring," Proc. SPIE 3998, pp. 125–134 (2000).

14. Conrad, U.S. Pat. No. 5,963,329.

15. McNeil, U.S. Pat. No. 5,867,276.

16. Xu, WO 99/45340.

17. Handbook of Optics, Second Edition, Volume 2, Optical Society of America (1995).

18. "Formulation and comparison of two recursive matrix algorithms for modeling layered diffraction gratings", Journal of the Optical Society of America, Vol. A 13, No. 5, May 1996.

BRIEF SUMMARY

The invention is a method for measuring parameters of interest of a sample comprising a diffractive structure, wherein the method employs a database-search technique in combination with interpolation to avoid the tradeoff between measurement resolution and accuracy. Following is a summary outline of the steps of the method, which will later be individually described in more detail. (The steps need not be performed in the exact order indicated here, except to the extent that dependencies between steps constrain their order.)

First, a theoretical model is provided, from which a theoretical optical response characteristic of the diffractive structure is calculable as a function of a set of one or more "interpolation parameters" corresponding to measurement parameters. The theoretical model comprises two primary components: a method for translating any trial set of interpolation parameter values into a computer-representable model of the diffractive structure (including its optical materials and geometry), and a method for numerically simulating electromagnetic interactions within the diffractive structure to calculate the theoretical response characteristic.

Next, a database of "interpolation points" and corresponding optical response characteristics is generated. Each interpolation point is defined by a specific interpolation parameter set consisting of specific values of the interpolation parameters. The theoretical model is applied to each interpolation point to calculate its corresponding theoretical optical response characteristic, which is stored in the database.

The database is used by an "interpolation model", which calculates an interpolated optical response characteristic as a function of the interpolation parameter set. The interpolation model provides an approximation to the theoretical model, but without the computational overhead. Given any trial interpolation parameter set within a defined parameter domain, the interpolation model computes an approximate corresponding optical response characteristic by interpolating (or perhaps extrapolating) on the database. (The parameter domain is typically limited by the database, although extrapolation can sometimes be used to extend the domain outside of the database limits. The term "interpolation" can be broadly construed herein to include extrapolation.) The diffractive structure's internal geometry need not be modeled, and electromagnetic interactions within the structure need not be simulated, in the interpolation model. Thus the computational overhead of direct theoretical modeling of the diffractive structure is avoided. The interpolation model represents a substantially continuous function mapping the interpolation parameter set to the optical response characteristic—it does not exhibit the discontinuities or discretization of prior-art methods such as range-splitting and MMSE. Furthermore, although the interpolation is an approximation, the interpolated optical response characteristic accurately matches the theoretical optical response characteristic at the interpolation points represented in the database. Thus it does not suffer the accuracy limitation of prior-art functional approximation methods. (The term "interpolation" broadly connotes a fitting function that fits the interpolation points. A portion of the fitting function might actually be extrapolated, so in this context the distinction between "interpolation" and "extrapolation" is not significant.)

The interpolation model is used by a fitting optimization algorithm that determines measurement parameters of a sample based on a measured optical signal characteristic of the sample. The theoretical optical response characteristic, which is approximated by the interpolation model, does not necessarily correspond directly to the optical signal characteristic or to a measurable quantity. However, a predicted optical signal characteristic is calculable from the optical response characteristic by means of a computationally efficient algorithm that, like interpolation, does not require that the diffractive structure's internal geometry be modeled or that electromagnetic interactions within the structure be simulated. The optimization algorithm automatically selects a succession of trial interpolation parameter sets, applies the interpolation model to calculate corresponding interpolated optical response characteristics, and from these calculates corresponding predicted optical signal characteristics, which are compared to the measured optical signal characteristic. The algorithm selects the trial parameter sets, based on a comparison error minimization method, to iteratively reduce a defined comparison error metric until a defined termination criterion is satisfied.

The measured optical signal characteristic is acquired with a measurement instrument comprising an optical sensor system, which detects radiation diffracted from the sample. The instrument further comprises computational hardware that applies the fitting optimization algorithm to measured signal data and generates measurement results. Subsequent to results generation, the instrument may also generate a computational or graphical representation of the diffractive structure's geometry. However, this representation is not necessarily required to calculate a corresponding predicted optical response or signal characteristic, and it need not correspond to a particular parameter set in the database.

DETAILED DESCRIPTION

The Measurement Instrument:

The measurement instrument comprises a radiation source, illumination optics for conveying the radiation to a measurement sample, collection optics for conveying radiation reflected or diffracted from the sample to an optical sensor system, and computational hardware that controls the instrument and translates optical signal data from the sensor system into measurement results. Typically, the instrument collects signal data as a function of one or more control variables such as wavelength, illumination and collection directions (each direction being characterized by polar and azimuthal angles relative to the sample), illumination polarization state, and the collection optics' polarization characteristics. An instrument may scan a control variable or may have multiple sensor channels that simultaneously sample multiple values of the variable. (For example, the illumination wavelength may be scanned, or the system may use broadband illumination in conjunction with a spectrometer detector to simultaneously sense multiple wavelength signals.) Typically, each sensor channel responds to radiation comprising a non-zero range of wavelengths, angles, and polarization states, and the fitting optimization algorithm may need to take this into account to obtain a good fit between predicted and measured signal characteristics.

The above description covers a variety of instruments associated with different measurement types (scatterometry, spectroscopy, ellipsometry, and hybrid types). Different "signal" characteristics are associated with these various applications (e.g. reflectivity versus incidence angle for scatterometry, reflectivity versus wavelength for spectroscopy, and ellipsometric parameters such as psi and delta, or Stokes vector coefficients, for ellipsometry). But at a fundamental level all of these measurement types reduce to translating sensor signal data into measurement results, and the generic database interpolation method of the present invention applies equally well to all of these measurement types.

Figure 3A:
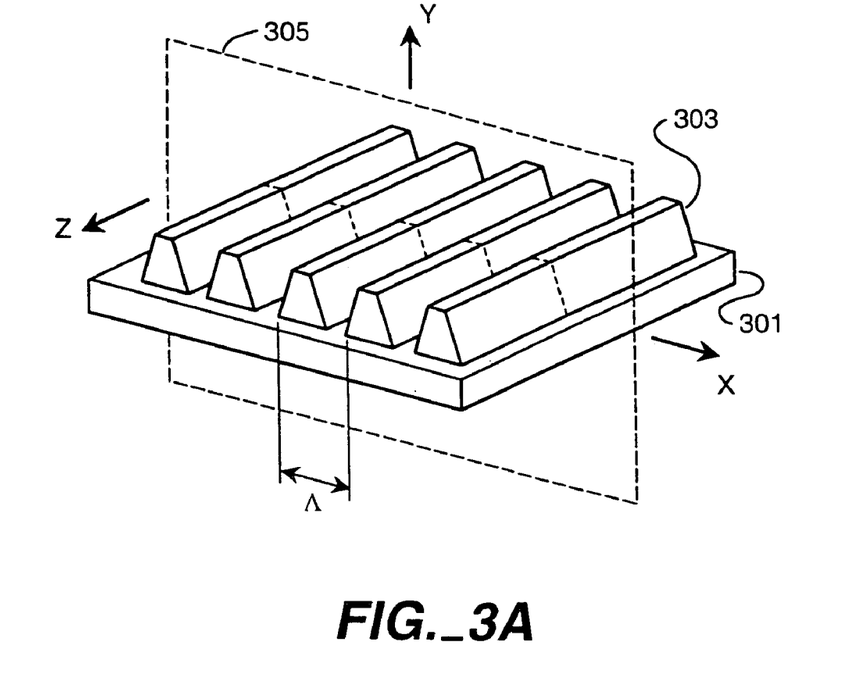
FIG. 3A illustrates a measurement sample comprising a diffractive, line-space grating structure.

The Measurement Sample:

In typical applications, the measurement sample is a periodic, line-space grating structure whose geometry is invariant with respect to translation in a particular direction. For example, FIG. 3A illustrates a line-space structure comprising grating lines 303 formed on a flat substrate 301. The structure is translationally invariant in the Z direction, and it has a periodicity dimension A in the X direction. The structure geometry is fully characterized by its two-dimensional cross-section in an X-Y plane 305.

Figure 3B:
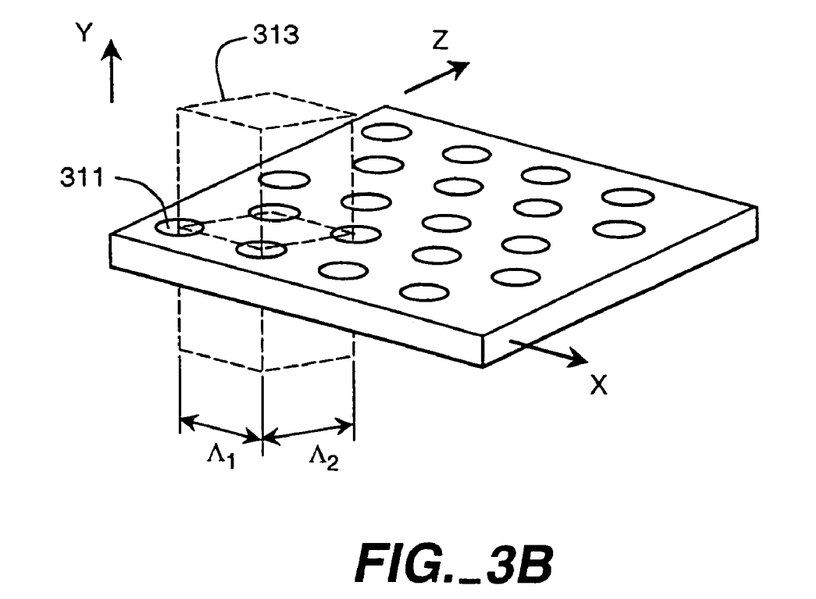
FIG. 3B illustrates a diffractive structure comprising a two-dimensional array of holes.

FIG. 3B illustrates another type of measurement sample comprising a two-dimensional array of holes 311 in a substrate. The geometry can be described in terms of a "grating cell" 313 which is repeated periodically in the X-Z plane, and is characterized in terms of two fundamental periods, $\Lambda_1$ and $\Lambda_2$.

Periodic structures such as those illustrated in FIGS. 3A and 3B have the property that, when illuminated by a narrow beam of radiation, the back-scattered radiation comprises a discrete set of narrow beams, or "diffracted orders". These orders include the specularaly reflected ("zeroth order") component of the scattered radiation. Generally, structures with smaller periods produce fewer orders, and if the periodicity is sufficiently fine no orders other than the zeroth order will propagate from the structure. The measurement instrument may be configured to selectively exclude, or accept, a particular diffracted order or orders. In typical applications, only the zeroth order is used.

Figure 4:
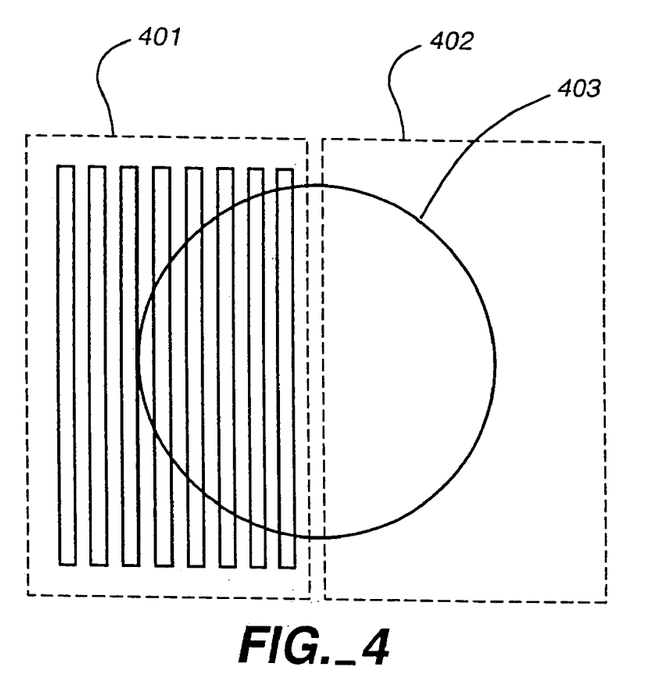
FIG. 4 illustrates a plan view of a sample comprising two reflecting zones.

The method of the present invention is not limited to strictly periodic structures such as those illustrated in FIGS. 3A and 3B. It is also applicable to quasi-periodic or aperiodic sample types. For example, FIG. 4 illustrates a plan view of a sample comprising two reflecting zones, a first zone 401 comprising a diffractive line-space structure, and a second adjacent zone 402 that is laterally homogeneous. The illuminating radiation covers a measurement spot 403 that straddles both zones.

Figure 5A:
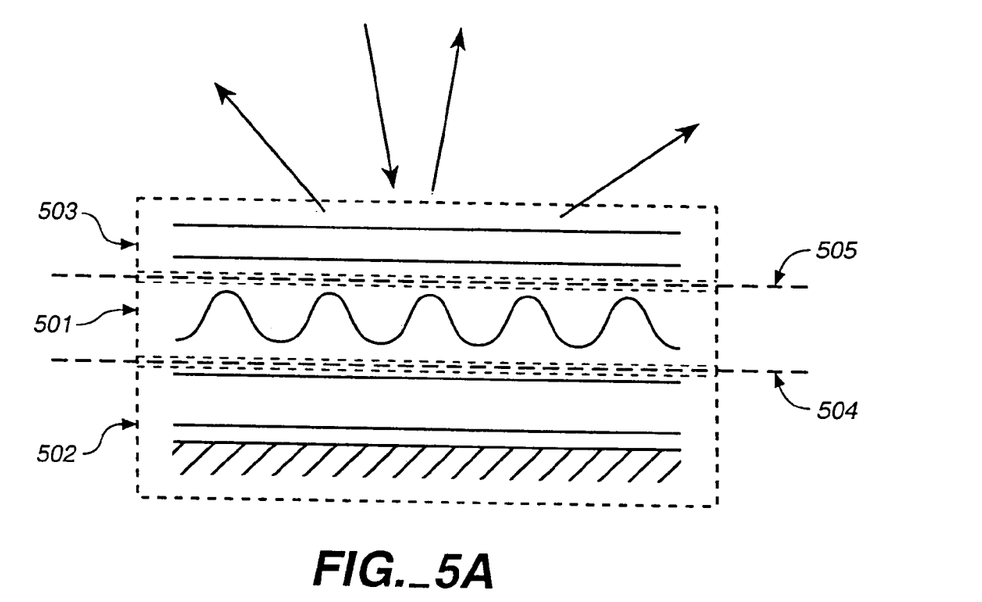
FIG. 5A illustrates a measurement sample comprising a layered structure with one diffractive layer.
Figure 5B:
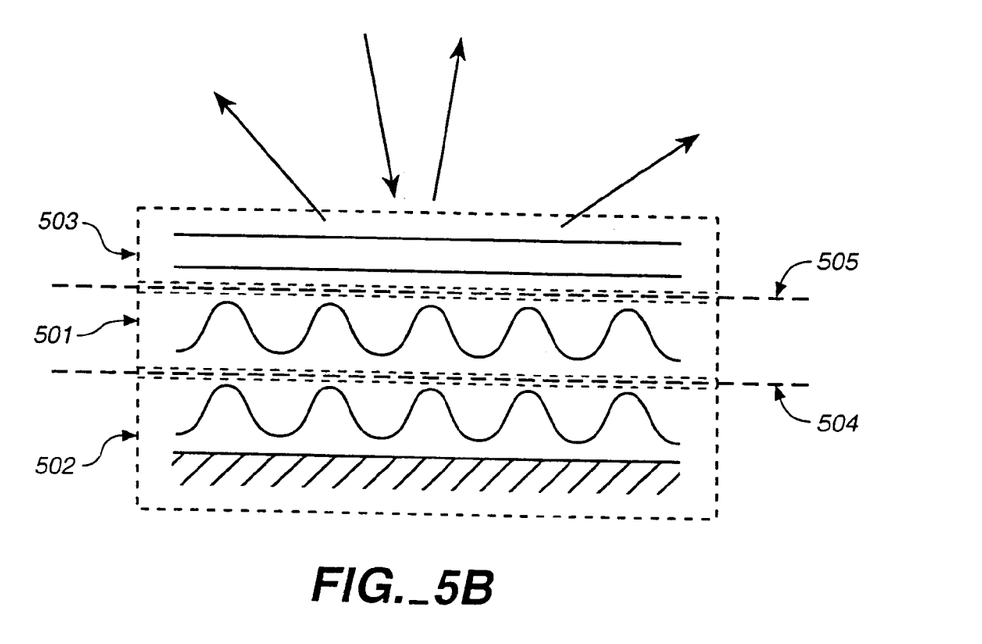
FIG. 5B illustrates a measurement sample comprising a layered structure with two diffractive layers.

The measurement sample is typically a layered structure, such as that illustrated cross-sectionally in FIG. 5A or 5B. FIG. 5A illustrates a sample comprising a diffractive structure 501 sandwiched between a non-diffractive substructure 502 and a non-diffractive superstructure 503. The non-diffractive structures may each comprise multiple layers, which may be homogeneous or may have refractive index gradients, but which are typically laterally homogeneous (i.e., the refractive index only varies in the direction normal to the substrate). Conversely, FIG. 5B illustrates a sample type in which the substructure 502 contains a second diffractive layer.

Depending on how the method of the invention is applied, the subject "diffractive structure" of the method may be interpreted as the sample as a whole (or more specifically, a portion of the sample in the vicinity of the measurement spot), or as a component of the sample. For example, the subject diffractive structure could be the diffractive zone 401 in FIG. 4, or the diffractive layer 501 in FIG. 5A or 5B.

The Theoretical Model:

There are two basic components of the theoretical model: A model of the diffractive structure (including its optical materials and geometry), and a model of the electromagnetic interactions within the diffractive sample, which determine the sample's diffractive optical properties. The subject theoretical model of the invention method does not necessarily characterize the sample as a whole—it characterizes the subject diffractive structure, which may only be one of a number of components of the sample; and the subject theoretical model may itself be a component of a broader theoretical model that characterizes the whole sample.

The measurement sample structure is typically represented computationally as a function of one or more "sample parameters" (e.g., linewidth, layer thicknesses, material parameters), some of which are known in advance and some of which are determined by measurement. Of the latter "measurement parameters", some or all are associated with the subject diffractive structure—these are termed "interpolation parameters" herein. The theoretical model comprises a functional mapping that associates an ordered set of interpolation parameter values (one value for each interpolation parameter) with a corresponding diffractive structure configuration (materials and geometry). Given any particular interpolation parameter set, the theoretical model generates a computational representation of the diffractive structure; it performs a numerical simulation of electromagnetic propagation of radiation through the interior of the diffractive structure; and based on the electromagnetic simulation it calculates a theoretical optical response characteristic of the diffractive structure. This response characteristic may, in some applications, need to be combined with optical response characteristics of other components of the sample (e.g. the non-diffractive structure 402 of FIG. 4 or the substructure 502 or superstructure 503 of FIG. 5A or 5B) to characterize the whole sample. This combining process may include modeling electromagnetic interactions at the interfaces between the components (i.e., applying boundary conditions). However, the processes of generating the other components' response characteristics and combining them with the subject diffractive structure's response characteristic do not require that the diffractive structure's internal geometry (e.g., profile shape) be modeled or that the electromagnetic propagation within the diffractive structure be simulated.

The optical response characteristic could comprise a measurable quantity such as reflectivity. However, in the preferred embodiments the response characteristic comprises complex reflectance coefficients (or generalizations of the complex reflectance coefficient, which will be discussed below), which are not directly measurable. (The measurable reflectivity is a real-valued quantity that is calculable from the complex reflectance coefficient.) An advantage of this approach is that individual components of the sample, such as the subject diffractive structure, can be represented by separate response characteristics, which can be simply combined (during a real-time measurement process, if necessary) to calculate a predicted optical signal characteristic of the sample. (There is also another advantage relating to interpolation accuracy that will be discussed later.)

The "signal characteristic" is a measurable quantity that can be obtained from, or is calculable from, a signal generated by the measurement instrument's optical sensor system. The signal characteristic depends on the instrument's optical characteristics, as well as the sample. For example, the polarization characteristics of the illuminating radiation or of the collection optics may need to be taken into account in calculating the predicted signal. The instrument's optical characteristics, such as polarization, may be controlled during data acquisition, and may be represented by instrument calibration quantities that can vary from instrument to instrument. Typically, the measurable signal characteristic depends on the entire sample structure and the instrument characteristics—it cannot generally be separated into components associated with individual sample components or with the instrument, whereas such a separation can often be performed with complex reflectance-type quantities. (Reflecting samples that exhibit significant polarizing properties can be characterized in terms of a "reflectance Jones matrix", which is a generalization of the complex reflectance coefficient. See Section 27.7 in Ref. 17 for a description of the Jones matrix.)

A possible use for the present invention can be illustrated with reference to co-pending patent application, "Method of Measuring Meso-Scale Structures on Wafers" (App. Ser. No. 09/735,286, filed Dec. 11, 2000), the disclosure of which is incorporated by reference herein. This method applies to a measurement in which the measurement spot straddles multiple reflecting zones with different reflectance properties, and the predicted signal characteristic of the sample is calculated as a partially coherent mixture of the individual zones' reflectivities. The partial coherence mixing model requires the complex reflectance coefficients $r_1, r_2, \ldots$ of the individual zones. An embodiment of the mixing model described in the Ser. No. 09/735,286 application is reproduced below as Eq. 3, $$R = \left(\sum_j A_j |r_j|^2\right) + \left(\sum_{j,k(j<k)} B_{j,k} \mathrm{Re}[r_j r_k^*] + C_{j,k} \mathrm{Im}[r_j r_k^*]\right) \quad \text{Eq. 3}$$

The A, B, and C terms in this expression are "mixing coefficients" which may be sample parameters or functions of sample parameters. (They may also be functions of the instrument's optical properties.) The r terms (complex reflectance coefficients) are the optical response characteristics of the reflecting zones. The mixing model calculates R, an "effective reflectivity", which corresponds to a measurable signal characteristic of the sample.

In the context of the present invention, one of the reflecting zones of the mixing model would correspond to the invention's subject diffraction structure. For example, FIG. 4 illustrates a two-zone sample comprising a diffracting zone 401 and a non-diffracting zone 402. Denoting by $r_1$ the complex reflectance coefficient of the diffractive structure, the subject theoretical model of the present invention calculates $r_1$ as a function of interpolation parameters. This theoretical model is a component of a broader theoretical model—the mixing model—that computes the sample's signal characteristic R by combining $r_1$ with the optical response characteristics of the other adjoining zone or zones, in accordance with Eq. 3.

Multi-layer structures such as those illustrated in FIGS. 5A and 5B can be similarly partitioned into separate components (layers, in this case), each represented by its own optical response characteristic. Theoretical models for these types of structures typically represent the illumination and diffracted radiation as plane-wave expansions. A plane wave is a simplifying mathematical abstraction that is infinite in spatial and temporal extent. Each plane wave has a specific direction of propagation, wavelength, and polarization state. When a periodic structure is illuminated with a plane wave, it scatters the illumination into a discrete set of plane waves, or "diffraction orders", which may include both transmitted and reflected orders. The undeviated transmitted order is termed the "zeroth transmitted order," and the specularly reflected order is termed the "zeroth reflected order." The ratios of the diffracted orders' complex amplitudes to the incident plane wave's complex amplitude are termed "complex scattering coefficients". (These include reflectance scattering coefficients for reflected orders and transmittance scattering coefficients for transmitted orders). Each order is characterized by two scalar scattering coefficients corresponding to two constituent polarization components of the order (e.g., orthogonal linear polarization components). Furthermore, each of these coefficients depends on the polarization state of the incident illumination, so considering two independent incident polarization states, each order will actually have four associated scalar scattering coefficients corresponding to any particular wavelength and incidence direction.

A theoretical optical model of the sample will calculate the complex scattering coefficients of one or more diffracted orders as a function of the incident plane wave's direction, wavelength, and polarization state. If the sample structure as a whole is regarded as the subject diffractive structure of the present invention, the aggregation of the individual complex scattering coefficients could constitute the structure's optical response characteristic. If the subject diffractive structure is an individual layer component in a layered structure, such as element 501 in FIG. 5A or 5B, the optical response characteristic could comprise a "scattering matrix", which represents a linear relationship between complex amplitudes of electromagnetic field components at the diffractive layers two bounding surfaces, 504 and 505. Other layers in the sample may be similarly represented by scattering matrices. The multiple scattering matrices of the different layers may be combined to form a composite scattering matrix for the entire sample, from which the scattering coefficients are readily obtained. For example, an algorithm for combining scattering matrices (S-matrices) of adjacent layers is described in Ref. 18 (see especially equation 15A). Either of the S-matrix or R-matrix formulations described in this published article could be used to define a diffractive layer's optical response characteristic. The process of combining the optical response characteristics (either S-matrices or R-matrices) is much simpler and quicker than the computation of the layers' response characteristics themselves (at least for diffractive layers), and could potentially be performed during a real-time measurement process.

The subject theoretical model of the invention could be a component of a hierarchy of theoretical optical models. For example, the subject theoretical model could calculate an optical response characteristic (e.g., an S-matrix) characterizing diffractive layer 501 in the multilayer structure of FIG. 5A or 5B. This model would be a component of a second-tier theoretical model that calculates an optical response characteristic for the entire multilayer structure. This structure may represent just one of multiple reflecting zones, such as zone 401 in FIG. 4, and the structure's corresponding second-tier theoretical model may be a component of a third-tier theoretical model (e.g. a mixing model) that calculates a diffraction response characteristic for the entire multi-zone measurement sample.

The Interpolation Database:

The theoretical model is applied to each of a plurality of "interpolation points", each point defined by a specific interpolation parameter set consisting of specific values of the interpolation parameters. For each interpolation point, a corresponding optical response characteristic of the diffractive structure is calculated and stored in the database. Typically, each stored optical response characteristic comprises a plurality of complex reflectance coefficients or scattering matrices associated with different illumination wavelengths, incidence directions, and polarization states, but all associated with the same diffractive structure configuration (materials and geometry). The computational representation of the associated structure geometry (e.g., profile shape) is not required for subsequent measurement processes and need not be stored in the database.

The Interpolation Model:

The interpolation model uses the database to estimate the optical response characteristic for interpolation parameter sets that are not necessarily represented in the database. The interpolation model defines a continuous function relating any trial interpolation set to a corresponding optical response characteristic, and in a preferred embodiment the response function is also smooth (i.e., continuously differentiable). Of course, the continuity and smoothness may be limited by practical limitations such as data discretization, but the function is "substantially continuous" in the sense that any actual discontinuities are insignificant in comparison to the data discretization in the database. Furthermore, the interpolation function substantially matches the theoretical optical response characteristic at the database interpolation points, in the sense that any slight mismatch is insignificant from the perspective of measurement performance.

The interpolation function is defined over a parameter domain that typically covers the database interpolation points. The parameter domain may possibly be extended by extrapolation. The accuracy of extrapolation is usually very poor, but in some cases the functional dependence of the optical response characteristic on a particular interpolation parameter may be very nearly linear, in which case extrapolation may be reliably applied to that parameter.

Figure 6A:
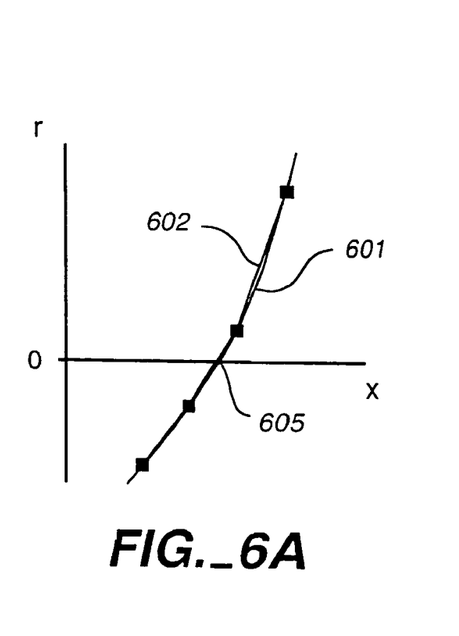
FIG. 6A illustrates a plot of a measurement sample's complex reflection coefficient r as a function of a measurement parameter, x.
Figure 6B:
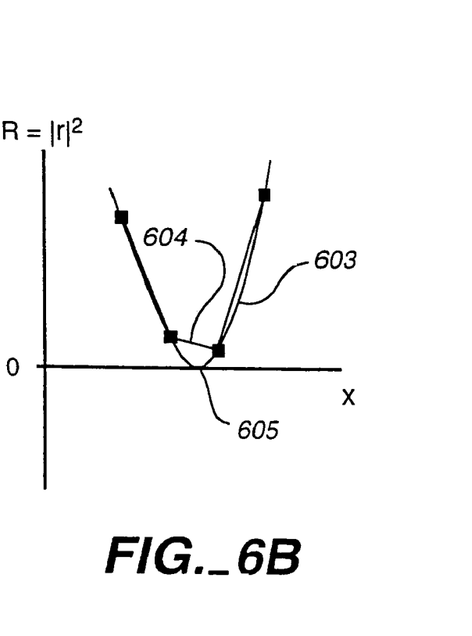
FIG. 6B illustrates the reflectivity signal, $R = r^2$ corresponding to the reflection coefficient of FIG. 6A.

The interpolation function will exhibit accuracy errors at interpolation parameter sets that do not correspond to interpolation points, but these errors can be mitigated by interpolating on an optical response characteristic, such as complex reflectance, that is related to the (complex-valued) electromagnetic field amplitudes, rather than a signal-related response characteristic. This principle is illustrated in FIGS. 6A and 6B. FIG. 6A illustrates a plot of a measurement sample's complex reflection coefficient r (for some particular wavelength, incidence direction, and polarization state) as a function of a measurement parameter, x (e.g., linewidth). For the purpose of illustration, the theoretical plot 601 of r versus x is illustrated as real-valued, although in general it would be complex-valued. A linear interpolation of r versus x between four interpolation points is illustrated as the piecewise-linear plot 602. FIG. 6B illustrates the reflectivity signal, $R=r^2$, as plot 603, and the linearly-interpolated signal as plot 604. In the vicinity of the zero crossing 605 the signal plot 603 is very nonlinear, resulting in a poor interpolation fit; whereas the interpolation fit on the complex reflection coefficient is very accurate near the zero crossing. (The accuracy of the signal interpolation could be improved by using a nonlinear interpolating function. But regardless of what interpolation method is used, the interpolation fit would generally be better when applied to complex reflection coefficient.)

Figure 7:
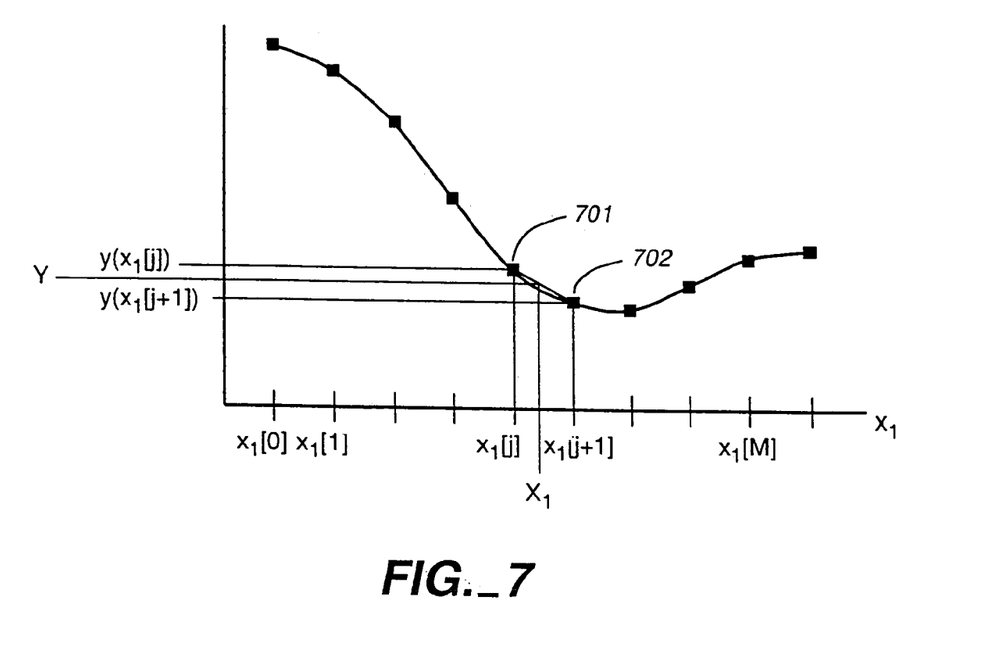
FIG. 7 illustrates piecewise-linear interpolation on an optical response characteristic.

The simplest form of interpolation is piecewise-linear interpolation, which is illustrated in FIG. 7. In this example, a single, scalar-valued optical response characteristic y is interpolated over a single, scalar-valued measurement parameter $x_1$. The parameter is sampled in the database at uniformly-spaced parameter values, $x_1[0], x_1[1], \ldots x_1[M]$ (wherein M is the number of sampling intervals), and y is linearly interpolated between the database values. The $\{x_1, y\}$ pairs represented in the database are the "interpolation points", two of which are indicated in the figure as 701 and 702. Given an arbitrary interpolation parameter value $X_1$, the corresponding interpolated y value, denoted Y, is calculated by the following procedure. First, assuming that $X_1$ is within the sampling range ($x_1[0] \leq X_1 < x_1[M]$), find an interpolation interval containing $X_1$, $$x_1[j] \leq X_1 < x_1[j+1] \ (0 \leq j < M) \qquad \text{Eq. 4}$$

(If $X_1$ is not within the sampling range Eq. 4 cannot be satisfied, but Y can be extrapolated from the interpolation interval that is closest to $X_1$. The following mathematical formalism applies equally well to extrapolation.) Having selected the interpolation (or extrapolation) interval, initialize quantities $C_0[0]$ and $C_0[1]$ to the interval's $x_1$ limits, $$C_0[0]=x_1[j],\ C_0[1]=x_1[j+1] \qquad \text{Eq. 5}$$

Then calculate an interpolation fraction t and interpolation coefficients $C_1[0]$ and $C_1[1]$, $$t = \frac{X_1 - C_0[0]}{C_0[1] - C_0[0]} \qquad \text{Eq. 6}$$

$$C_1[0] = 1 - t,\ C_1[1] = t \qquad \text{Eq. 7}$$

and apply these coefficients to the database data to obtain Y, $$Y = C_1[0] y(x_1[j]) + C_1[1] y(x_1[j+1]) \qquad \text{Eq. 8}$$

($y(x_1[j])$ and $y(x_1[j+1])$ are obtained from the database.)

For the general case of N-dimensional interpolation, the independent variable x is vector-valued, $$x = \{x_1, x_2, \ldots x_N\} \qquad \text{Eq. 9}$$

(This vector is the "interpolation parameter set".) Also, the optical response characteristic y may be a composite entity such as a vector or a matrix. (The components of y may, for example, correspond to different scattering matrix coefficients and different combinations of wavelength, incidence direction, and polarization.) Each component $x_i$ of x is sampled in the database at uniformly-spaced values $x_i[0]$, $x_i[1]$, ... $x_i[M_i]$ (wherein $M_i$ is the number of sampling intervals for $x_i$). The database parameter range comprises a multi-dimensional array of "sampling grid cells", each cell being bounded in each i-th dimension by two successive parameter values $x_i[j_i]$ and $x_i[j_i+1]$. The interpolation algorithm approximates y as a multilinear function of x in each grid cell. Given an arbitrary interpolation parameter set $X=\{X_1, X_2, \ldots X_N\}$, the corresponding interpolated y value, denoted Y, is calculated by the following procedure. First, find a grid cell containing X, $$x_i[j_i] \leq X_i < x_i[j_i+1] \qquad \text{Eq. 10}$$

(for each i, $1 \leq i \leq N$; and some $j_i$, $0 \leq j_i < M_i$)

(As in the one-dimensional case, if X is outside of the parameter sampling range, Y can be extrapolated from the grid cell nearest to X.) Next, initialize vector quantities $C_0[k_1, k_2, \ldots k_N]$ to the corresponding grid cell limits, $$C_0[k_1, k_2, \ldots k_N] = \{x_1[j_1+k_1], x_2[j_2+k_2], \ldots\} \qquad \text{Eq. 11}$$

(for each $k_i = 0$ or 1, $1 \leq i \leq N$)

This initializes an iteration wherein, at step i, $C_i[k_1, k_2, \ldots k_N]$ represents linear interpolation coefficients of y with respect to parameter values $x_1, \ldots x_i$, which are spatially sampled at the grid cell limits of parameter values $x_{i+1}, \ldots x_N$. For each i=1 ... N, $C_i[k_1, k_2, \ldots k_N]$ is generated from $C_{i-1}[k_1, k_2, \ldots k_N]$ by applying the one-dimensional interpolation method to the i-th parameter dimension ($x_i$), $$t_i = \frac{X_i - C_{i-1}[\ldots k_{i-1}, 0, k_{i+1}, \ldots]}{C_{i-1}[\ldots k_{i-1}, 1, k_{i+1}, \ldots] - C_{i-1}[\ldots k_{i-1}, 0, k_{i+1}, \ldots]} \qquad \text{Eq. 12}$$

$$C_i[\ldots k_{i-1}, 0, k_{i+1}, \ldots] = 1 - t_i,$$
$$C_i[\ldots k_{i-1}, 1, k_{i+1}, \ldots] = t_i \qquad \text{Eq. 13}$$

These coefficients are applied to the database data to obtain Y, $$Y = \sum_{k_1, k_2, \ldots} C_N[k_1, k_2, \ldots] y(\{x_1[j_1+k_1], x_2[j_2+k_2], \ldots\}) \qquad \text{Eq. 14}$$

The derivatives of the interpolated quantity Y with respect to $X_i$ can be easily calculated using the above formalism. As will be seen later, the derivative information can be used to significantly enhance the runtime performance of the fitting optimization algorithm.

Improved interpolation accuracy can be obtained by using a multi-cubic, rather than multilinear, interpolating function in each grid cell. Alternatively, a hybrid approach may be used in which linear interpolation is used for some parameters, and cubic interpolation is used for others.

The one-dimensional cubic interpolation case can be illustrated with reference to FIG. 7. Within the interpolation interval $x_1[j] \leq X_1 < x_1[j+1]$ the interpolated value Y is approximated as a cubic function of $X_1$. The coefficients of the cubic function are chosen so that the interpolation fits both the database y values and the finite-difference derivatives of y with respect to $x_1$ at the interpolation interval boundaries. The derivative $y'(x_1[j])$ at point $x_1[j]$ is estimated as $$y'(x_1[j]) \cong \frac{y(x_1[j+1]) - y(x_1[j-1])}{x_1[j+1] - x_1[j-1]} \qquad \text{Eq. 15}$$

This assumes that point j is an interior point, i.e. $0 < j < M$. Since the derivative cannot be estimated by this method at the boundary points (j=0 or j=M), cubic interpolation is not applied within boundary intervals. Instead, three-point quadratic interpolation may be applied in the boundary intervals.

The one-dimensional cubic interpolation algorithm proceeds as follows. First, $X_1$ is assumed to be within an interior sampling interval, $$x_1[j] \leq X_1 < x_1[j+1] \quad 1 \leq j < M-1 \qquad \text{Eq. 16}$$

The following database sampling values of $x_1$ are defined, $$C_0[-1] = x_1[j-1],\ C_0[0] = x_1[j],\ C_0[1] = x_1[j+1],\ C_0[2] = x_1[j+2] \qquad \text{Eq. 17}$$

Then the following quantities are calculated, $$t = \frac{X_1 - C_0[0]}{C_0[1] - C_0[0]} \qquad \text{Eq. 18}$$

$$C_1[-1] = -\frac{1}{2}t + t^2 - \frac{1}{2}t^3 \qquad \text{Eq. 19}$$

$$C_1[0] = 1 - \frac{5}{2}t^2 + \frac{3}{2}t^3, \qquad \text{Eq. 20}$$

$$C_1[1] = \frac{1}{2}t + 2t^2 - \frac{3}{2}t^3 \qquad \text{Eq. 21}$$

$$C_1[2] = -\frac{1}{2}t^2 + \frac{1}{2}t^3 \qquad \text{Eq. 22}$$

and the interpolated Y value is obtained, $$Y = C_1[-1]y(x_1[j-1]) + C_1[0]y(x_1[j]) + C_1[1]y(x_1[j+1]) + C_1[2]y(x_1[j+2]) \qquad \text{Eq. 23}$$

The N-dimensional interpolation algorithm described previously can be modified to accommodate cubic interpolation on a particular parameter $x_i$ (or any combination of parameters) as follows: First, the $j_i$ index appearing in Eq. 10 should be in the range $1 \leq j_i < M_i - 1$. (This is for the specific subscript i corresponding to $x_i$.) The corresponding index $k_i$ appearing in Eq's. 11 and 14 takes on the values $k_i = -1, 0, 1,$ or 2. Eq. 12 applies without change, but Eq. 13 is modified to define the four quantities $C_i[\ldots k_{i-1}, -1, k_{i+1}, \ldots]$, $C_i[\ldots k_{i-1}, 0, k_{i+1}, \ldots]$, $C_i[\ldots k_{i-1}, 1, k_{i+1}, \ldots]$, and $C_i[\ldots k_{i-1}, 2, k_{i+1}, \ldots]$ by generalizing Eq's. 19–22 (i.e, substitute these four expressions for the respective left-hand terms in Eq's. 19–22, and substitute $t_i$ for t).

As noted above, the cubic interpolation method does not apply in boundary intervals ($j_i=0$ or $j_i=M_i-1$). Assuming that $x_i$ is sampled at three or more points ($M_i \geq 2$), a three-point quadratic fit may be applied in the boundary intervals. For example, in the one-dimensional case, if $j=0$ the term $y(x_1[j-1])$ in Eq. 23 is undefined (i.e., not in the database), so the $C_1[-1]$ term is omitted and the $C_1[0]$, $C_1[1]$, and $C_1[2]$ terms are quadratic functions of t with quadratic coefficients selected so that the interpolated Y value matches the database when $X_1$ is equal to $x_1[0]$, $x_1[1]$, or $x_1[2]$. This fit function is used in the interval $x_1[0] \leq X_1 < x_1[1]$. (As in the case of linear interpolation, the quadratic fit function can be extrapolated for values $X_1 < x_1[0]$.) If cubic interpolation is applied in the adjacent interval ($x_1[1] \leq X_1 < x_1[2]$) the interpolated Y value will be both continuous and continuously differentiable (smooth) with respect to $X_1$ at $X_1 = x_1[1]$. (This is because the derivative of the cubic fit function at $X_1 = x_1[1]$ is defined by Eq. 15, which also happens to be an exact identity for any quadratic function.)

The interpolation coefficients ($C_N[k_1, k_2, \ldots]$) are preferably not pre-computed, but generated in real time during the measurement process so that the interpolation relies only on optical response data stored in the database. Furthermore, derivatives of Y with respect to X can also be computed in real time. The interpolation method does not require that any extraneous data such as interpolation coefficients or derivatives be stored in the database. (Such information could be stored in the database to improve measurement runtime efficiency, but the improvement would typically be minimal and would be offset by the increased database size and generation time.) Referring back to an example considered in the prior-art discussion, if the range of each parameter $x_1, \ldots x_N$ is divided into M sample intervals (i.e. M+1 sample points per parameter), the total number of interpolation points in the database would be $(M+1)^N$, compared to the $(N+1)M^N$ calibration points required by the prior-art example (range splitting). For large M and N, the method of the present invention would have an approximately N-fold advantage in database size over the prior art method.

The above interpolation methods represent preferred embodiments of the invention. Other interpolation methods, for example linear or quadratic interpolation on a triangular or simplex-shaped sampling grid, or multi-dimensional spline interpolation, could also be used. The above methods may appear to be constraining, in that parameters are all sampled at uniform intervals over a rectangular region of parameter space. However, the algorithm designer has a great degree of freedom in how the interpolation parameters are defined, which largely offsets this limitation. For example, rather than identifying a profile linewidth as an interpolation parameter, the linewidth can be represented as a nonlinear function of a uniformly-sampled interpolation parameter, with the functional mapping chosen so that small linewidths are sampled more finely than large linewidths. Many variant interpolation approaches are possible; within this realm of variation the primary distinguishing features of the interpolation method are that it defines a substantially continuous function of interpolation parameters over a parameter domain that includes the interpolation points, and the interpolated optical response characteristic substantially matches the theoretical optical response characteristic at the interpolation points.

The Fitting Optimization Algorithm:

The fitting optimization algorithm iteratively compares the measured optical signal characteristic of the measurement sample with a plurality of predicted optical signal characteristics determined from corresponding interpolated optical response characteristics to find a best-fit parameter set, which defines the measured parameters of the sample.

The predicted optical signal characteristic is determined from the interpolated optical response characteristic, which is obtained from the interpolation model. In some applications the "signal" and "response" characteristics may be one and the same, and this determination does not require additional calculations. More commonly, the optical response characteristic is a quantity or composition of quantities such as complex reflectance coefficients from which the signal characteristic is calculated in real time (i.e. after acquiring the measured signal). This calculation involves several steps. First, if the optical response characteristic represented in the interpolation database only characterizes a component of the sample (such as diffractive reflecting zone 401 in FIG. 4 or the diffractive layer 501 in FIG. 5A or 5B), the interpolated characteristic would need to be combined with optical response characteristics of other sample components to obtain a combined optical response characteristic of the sample as a whole. The other components' response characteristics might be similarly obtained from their own interpolation models, or might be obtained directly from theory in real time. (For example, a non-diffractive layer's optical response characteristic can be computed from theory very easily and quickly.)

Having determined the sample's optical response characteristic, this may need to be combined with instrument-related characteristics to obtain an optical response characteristic of the optical system comprising the measurement sample and the instrument optics. For example, polarizing properties of the instrument's illumination and collection optics may be separately represented by Jones matrices (or alternatively, Mueller matrices), which would be combined with the sample's response characteristic to calculate a Jones (or Mueller) matrix of the entire optical system (illumination optics, sample, and collection optics). If the polarization or other characteristics of the instrument are varied as the measurement signal is acquired, this calculation may be repeated for each of a number of instrument configurations. (For example, an ellisometer typically has a polarization-modulating element, and its measured signal characteristic is typically a composition of signals associated with various states of the modulating element.) The optical system's response characteristic is used to calculate the predicted signal characteristic by effectively simulating the electromagnetic field intensity on the optical sensor elements. Each sensor element may respond to radiation comprising a range of wavelengths or corresponding to a range of incidence or collection directions at the sample, so this calculation may comprise a summation over wavelengths or directions. (Depending on the instrument's optical coherence properties, the directional summation may represent a coherent, incoherent, or partially coherent superposition of optical response components corresponding to different incidence or collection directions.)

The instrument-related data that enters into the predicted signal calculation may include factors such as optical calibrations and the illumination source intensity, which vary between instruments and with time. But rather than incorporating all of these factors in the predicted signal characteristic, at least some of these factors are more typically applied in an inverse manner to the sensor signal data to obtain a measured signal characteristic such as an "effective" reflectivity or Stokes vector that has minimal instrument dependence and is primarily a function of only the sample. (Ideally, one would like to obtain a measured signal characteristic that has no instrument dependence. But this is not always possible, and measurement accuracy may suffer if the fitting optimization algorithm neglects the signal characteristic's instrument dependence.)

Conventionally, the signal characteristic comprises reflectivity data or ellipsometric quantities such as tan $\Psi$ and cos $\Delta$ (Ref's 12, 16), which characterize the sample independently of the instrument. However, there can be practical advantages to defining the signal characteristic to be a quantity that is more closely related to actual detector signal levels. For example, in the context of ellipsometry, tan $\Psi$ can exhibit singularities and cos $\Delta$ can exhibit sharp jumps or discontinuities that can affect the numerical stability and accuracy of the measurement algorithm. Furthermore, tan $\Psi$ and cos $\Delta$ will generally be statistically correlated, which complicates the fitting optimization algorithm. (The algorithm may need to take into account the covariance between tan $\Psi$ and cos $\Delta$.) These complications can be circumvented by basing the measurement on a signal characteristic that corresponds to, or is closely related to, actual sensor signal levels. The "Stokes vector" and "Mueller matrix" components (Ref 17, Sect. 22.14) are suitable signal characteristics, from this perspective. (The Mueller matrix for a conventional rotating-polarizer ellipsometer, for example, contains two independent, dimensionless factors, cos ($2\Psi$) and sin ($2\Psi$) cos ($\Delta$), which have a linear dependence on the sensor signals.) It is not always possible to calculate quantities such as reflectivity or conventional ellipsometric parameters from sensor signal data without resorting to idealistic—and inaccurate—assumptions about the measurement instrument characteristics, and some loss of measurement accuracy is inevitable when the signal characteristic is reduced to an instrument-independent form such these. However, one can define a signal characteristic such as "effective reflectivity" (e.g. R in Eq. 3) or an "effective Stokes vector", etc., which has some instrument dependence but nevertheless has a close semblance to the conventional quantity. (Typically, the "effective" quantity is a summation or average over reflecting zones, or over wavelengths or incidence directions.)

The predicted and measured optical signal response characteristics are compared, and the comparison fit error is typically quantified in terms of a "fit metric" such as a chi-square metric ($\chi^2$), which is defined as $$\chi^2 = \sum_j wt_j \left(y_j^{pred}(x) - y_j^{meas}\right)^2 \qquad \text{Eq. 24}$$

In this definition y denotes a measurable signal characteristic comprising multiple signal components $y_j$ (e.g. signals from different sensor elements or different instrument configurations); x denotes a set of measurement parameters (e.g., film thicknesses, linewidth, etc.); $y_j^{pred}(x)$ denotes the predicted signal for x; $y_j^{meas}$ represents the measured signal characteristic; and $wt_j$ is a non-negative weighting factor. An indicated previously, the definition of $y_j^{meas}$ may incorporate factors such as the instrument's optical calibrations and the illumination source intensity, as well as the sensor signal data. The definition of $y_j^{pred}(x)$ may also include such instrument-related factors, as well as the sample parameter dependence. The algorithm designer has some degree of freedom in allocating the instrument-related factors between $y_j^{meas}$ and $y_j^{pred}(x)$ (e.g., by applying a common additive shift or dividing a common factor out of both terms).

The $\chi^2$ metric has the property that is is always non-negative, and is zero if and only if there is a perfect match between $y_j^{pred}(x)$ and $y_j^{meas}$ for all j. The objective of a fitting optimization algorithm based on the $\chi^2$ metric is to find a measured parameter set x that minimizes $\chi^2$. If $wt_j$ is set to 1 in Eq. 24, $\chi^2$ is similar to the fit metric employed by MMSE algorithms; however measurement precision can be optimized by defining $wt_j$ to be the reciprocal variance of $y_j^{meas}$, $$wt_j = \frac{1}{\sigma^2 y_j^{meas}} \qquad \text{Eq. 25}$$

The $\chi^2$ definition in Eq.'s 24 and 25 assumes that the measured quantities $y_j^{meas}$ are statistically uncorrelated. It also assumes that the calculation of $y_j^{pred}(x)$ does not depend on experimental data (e.g. illumination source intensity data), at least not to the extent that significant statistical uncertainty is introduced into the $y_j^{pred}(x)$ terms. A more general definition of $\chi^2$ that accommodates these possibilities is $$\chi^2 = (y^{pred}(x) - y^{meas})^T (cov\ y^{pred}(x) + cov\ y^{meas})^{-1} (y^{pred}(x) - y^{meas}) \qquad \text{Eq. 26}$$

In this equation, $y^{pred}(x)$ and $y^{meas}$ are column matrices comprising the $y_j^{pred}(x)$ and $y_j^{meas}$ elements; cov $y^{pred}(p)$ and cov $y^{meas}$ are associated covariance matrices; and the "T" superscript indicates matrix transposition.

The fitting optimization algorithm, in a preferred embodiment, iteratively adjusts x to minimize $\chi^2$. In this context, x is a "trial measurement parameter set" (i.e. an ordered set of numeric values, one for each measurement parameter). x includes the "trial interpolation parameter set", the elements of which correspond to interpolation parameters. (x may also include other sample parameters that are not associated with the invention's subject diffractive structure.) The minimization method includes two stages, a preliminary "grid search", and subsequent "refinement".

Figure 8:
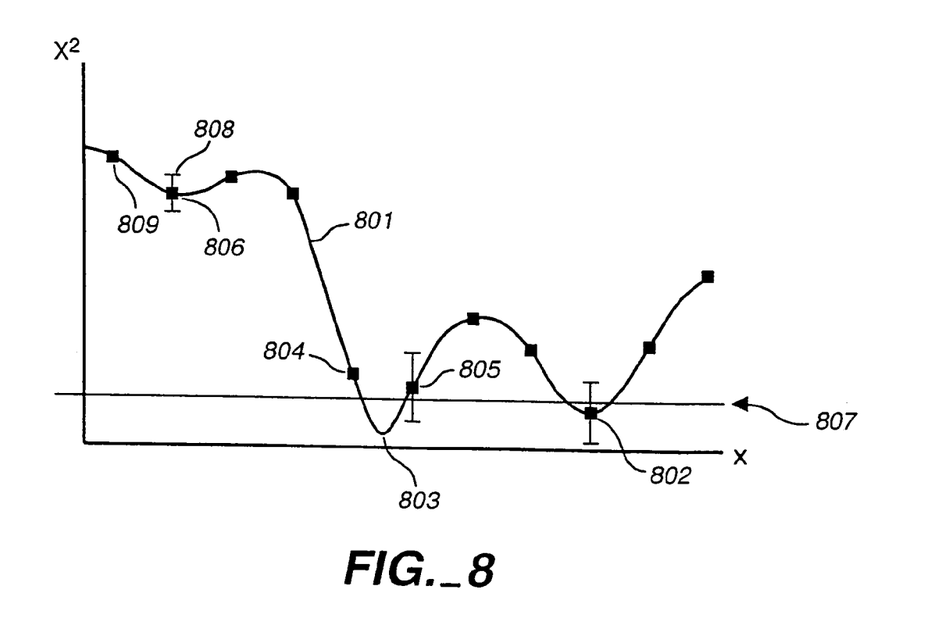
FIG. 8 illustrates the selection of trial parameter sets for refinement in the fitting optimization algorithm.

In the first stage, a multi-dimensional grid of trial measurement parameter sets is defined, and $\chi^2$ is calculated for every point x on the grid. (In this context "grid point" is synonymous with "trial measurement parameter set". The grid points may, in some embodiments, correspond to the database interpolation points.) One or more trial parameter sets are selected from the grid for subsequent refinement. FIG. 8 conceptually illustrates the selection process.

The grid search scans the grid points for parameter sets that could potentially be close to a global minimum of $\chi^2$ over a parameter domain that includes the grid points. It is not sufficient to just select the grid point with the lowest $\chi^2$ because, as illustrated in FIG. 8, this strategy could yield false results due to the grid's limited sampling density. For example, the curve 801 illustrates $\chi^2$ as a function of a scalar parameter value, x. Grid points (e.g. point 802) are represented as squares on curve 801. The lowest $\chi^2$ on the grid is at point 802; but the true minimum (and the correct x value) is located at point 803, which is between grid points 804 and 805.

To ensure that the grid search does not miss the global $\chi^2$ minimum, it first finds all local minima on the grid. In FIG. 8, the grid local minima are points 802, 805, and 806. The local minima search will typically find a large number of points, such as point 806, which have very poor fits and are obviously not near the correct solution. The bad points are filtered out-by applying a $\chi^2$ threshold criterion. But again, due to the database's limited sampling density, it is not sufficient to just exclude all points above the $\chi^2$ threshold.

For example, if this strategy were applied, the threshold level 807 in FIG. 8 would exclude the grid point 805 nearest the global minimum 803, but would accept the false minimum 802. This problem is avoided by determining an "uncertainty range" for each local minimum (such as range 808 for point 806), which represents a conservative estimate of how much $\chi^2$ can vary within a ±½ grid interval centered at the point, and filtering out only those points whose uncertainty ranges are entirely above the threshold. Each uncertainty range is centered at the corresponding grid point, and the height of the range is the maximum $\chi^2$ difference between the local minimum and any adjacent grid point. (For example, the height of range 808 is equal to the $\chi^2$ difference between points 806 and 809) In FIG. 8, the uncertainty range of points 802 and 805 both extend below the threshold 807, so these points would be accepted for subsequent refinement; whereas point 806 would be rejected. Grid points that pass the local minimum and $\chi^2$ threshold selection criteria are passed to the refinement stage.

The grid search strategy illustrated in FIG. 8 generalizes in a straightforward manner to the more general case where there are multiple measurement parameter values and x is a vector-valued entity spanning a multi-dimensional parameter search range. For this case $\chi^2$ is sampled on a multi-dimensional grid. Local minima are identified, and an uncertainty range for each minimum is determined, based on comparisons of each point's $\chi^2$ value with those of adjacent points (including diagonal adjacencies); and points whose uncertainty ranges extend at least partially below the $\chi^2$ threshold are selected for further refinement.

Each selected grid point is used as a "seed" for subsequent refinement. The refinement is performed by an automated minimization algorithm that adjusts x to minimize $\chi^2$. (In this process x is not limited to discrete points represented in the grid or in the interpolation database; it can be varied continuously within a defined parameter domain.) The minimization algorithm iterates from the seed value until a defined termination criterion is satisfied (e.g., until incremental changes in x, or in $\chi^2$, fall below a certain threshold). Some minimizers require only that an abstract interface to the $\chi^2$ function, along with parameter limits and termination thresholds, be provided. However, better runtime performance can be achieved by providing the minimizer a vector of individual fit errors, $\epsilon_j$, defined as $$\epsilon_j \sqrt{wt_j}(y_j^{pred}(x) - y_j^{meas}) \quad \text{Eq. 27}$$

Note that $\chi^2$ (Eq. 24) is just the sum-squared fit error, $$\chi^2 = \sum_j \epsilon_j^2 \quad \text{Eq. 28}$$

Suitable minimization algorithms include MATLAB's "lsqnonlin" routine or the IMSL "BCLSF/DBCLSF" or "BCLSJ/DBCLSJ" routines. The runtime performance can be further enhanced by providing the minimizer the first-order derivatives of $\epsilon_j$ with respect to the x components (measurement parameters), along with $\epsilon_j$ itself. A useful feature of the database interpolation method is that these derivatives can be easily computed, and the fitting optimization algorithm should preferably make use of the derivatives.

After running the refinement on each selected grid point, the refined result with the lowest $\chi^2$ is reported as the measurement result. In some embodiments, the refinement stage may be divided into several sub-stages using progressively more accurate (though more time-consuming) calculation models. For example, the refinement might be done first using a linear interpolation model for the optical response characteristic, and then (after initial termination criteria of the minimization algorithm have been met), the refinement may be continued using cubic interpolation. Also, some measurement parameters, such as material-related parameters, might be initially held fixed when the refinement is initiated, and then allowed to vary as the refinement approaches convergence.

What is claimed is:

1. A method of evaluating a diffracting structure formed on a semiconductor sample comprising the steps of:
    measuring actual optical response characteristics of the sample; and
    iteratively interpolating between interpolation points for the sample using an interpolation model, each interpolation point corresponding to a sample parameter set, wherein the interpolation model defines a substantially continuous function which intersects with the interpolation points in order to derive a set of interpolated optical response characteristics that best fit the actual optical response characteristics, in order to evaluate the sample.

2. A method as recited in claim 1, wherein the actual optical response characteristics are in the form of one or both of complex reflectance coefficients and scattering matrices.

3. A method as recited in claim 1, wherein the actual optical response characteristics include ellipsometric parameters.

4. A method as recited in claim 1, wherein said actual optical response characteristics are created and measured as a function of wavelength.

5. A method as recited in claim 1, wherein said interpolation model utilizes one or more of linear, multi-cubic, and quadratic functions.

6. A method of evaluating parameters of a diffracting structure formed on semiconductor samples comprising the steps of:
    calculating optical response characteristics for selected parameter sets, each set of parameters corresponding to an interpolation point;
    defining a continuous model of the optical responses as a function of the parameters that equals the optical responses at the interpolation points;
    receiving a measurement signal for a sample; and
    evaluating the parameters of the sample by iteratively fitting the measurement signal with the interpolation model.

7. A method as recited in claim 6, wherein the calculating comprises calculating one or both the complex reflectance coefficients and scattering matrices.

8. A method as recited in claim 6, wherein said measurement signal includes measurement information as a function of wavelength.

9. A method as recited in claim 6, wherein said measurement signal includes measurement information regarding reflectance of the sample.

10. A method as recited in claim 6, wherein said interpolation model comprises one or more of linear, multi-cubic, or quadratic functions.

11. A method as recited in claim 6, wherein fitting comprises calculating a theoretical optical signal from the model.

12. A method as recited in claim 6, wherein the actual optical response characteristics include ellipsometric parameters.

13. A method of evaluating a diffracting structure formed on a semiconductor sample comprising the steps of:
   receiving a measurement signal containing actual optical response characteristics of the sample; and
   iteratively interpolating between interpolation points for the sample using an interpolation model, each interpolation point corresponding to a sample parameter set, wherein the interpolation model defines a substantially continuous function which intersects with the interpolation points in order to derive a set of interpolated optical response characteristics that best fit the actual optical response characteristics, in order to evaluate the sample.

14. A method as recited in claim 13, wherein the actual optical response characteristics are in the form of one or both of complex reflectance coefficients and scattering matrices.

15. A method as recited in claim 13, wherein said actual optical response characteristics are created and measured as a function of wavelength.

16. A method as recited in claim 13, wherein said interpolation model utilizes one or more of linear, multi-cubic, and quadratic functions.

17. A method as recited in claim 13, wherein the actual optical response characteristics include ellipsometric parameters.

* * * * *